United States Patent
Simon et al.

(10) Patent No.: US 8,398,636 B2
(45) Date of Patent: Mar. 19, 2013

(54) HIP FRACTURE DEVICE WITH BARREL AND END CAP FOR LOAD CONTROL

(75) Inventors: Bernd Simon, Kiel (DE); Jakob Kemper, Kiel (DE); Carsten Hoffmann, Mönkeberg (DE)

(73) Assignee: Stryker Trauma GmbH (DE)

( * ) Notice: Subject to any disclaimer, the term of this patent is extended or adjusted under 35 U.S.C. 154(b) by 918 days.

(21) Appl. No.: 12/082,691

(22) Filed: Apr. 11, 2008

(65) Prior Publication Data

US 2008/0269752 A1    Oct. 30, 2008

Related U.S. Application Data

(60) Provisional application No. 60/925,399, filed on Apr. 19, 2007.

(51) Int. Cl.
*A61B 17/56* (2006.01)
(52) U.S. Cl. ............................................. 606/65; 606/67
(58) Field of Classification Search ................... 606/55, 606/57, 64–68, 282, 257, 291; 623/20.35–20.36
See application file for complete search history.

(56) References Cited

U.S. PATENT DOCUMENTS

| | | | |
|---|---|---|---|
| 2,397,545 A | 4/1946 | Hardinge | |
| 2,612,159 A | 9/1952 | Collison | |
| 2,628,614 A | 2/1953 | Briggs | |
| 2,631,584 A | 3/1953 | Purifacto | |
| 2,702,543 A | 2/1955 | Pugh et al. | |
| 2,761,444 A | 9/1956 | Luck | |
| 2,801,631 A | 8/1957 | Charnley | |
| 2,834,342 A | 5/1958 | Yost | |
| 3,029,811 A | 4/1962 | Yost | |
| 3,107,666 A | 10/1963 | Cecere et al. | |
| 3,374,786 A * | 3/1968 | Callender, Jr. | 606/65 |
| 4,236,512 A | 12/1980 | Aginsky et al. | |
| 4,432,358 A * | 2/1984 | Fixel | 606/66 |
| 4,438,762 A | 3/1984 | Kyle | |
| 4,465,065 A | 8/1984 | Gotfried | |
| 4,488,543 A | 12/1984 | Tomier | |
| 4,612,920 A | 9/1986 | Lower | |
| 4,621,629 A | 11/1986 | Koeneman | |
| 4,628,923 A | 12/1986 | Medoff | |

(Continued)

FOREIGN PATENT DOCUMENTS

| | | |
|---|---|---|
| DE | 918531 C | 9/1954 |
| DE | 931431 C | 8/1955 |

(Continued)

OTHER PUBLICATIONS

Osteon News 39 Brouchre, Comprehension Hip Screw.

*Primary Examiner* — Eduardo C Robert
*Assistant Examiner* — James Palmer
(74) *Attorney, Agent, or Firm* — Lerner, David, Littenberg, Krumholz & Mentlik, LLP

(57) ABSTRACT

A hip fracture device providing distance limited dynamization, load controlled dynamization and combinations of both dynamization methods by varying components. The hip fracture device includes a plate having a head portion and a shaft portion. A barrel projects from the head portion of the plate and a screw is inserted in the barrel. A friction pin is slidably connected with the screw, and an end cap is fixed to the head portion of the plate. The friction pin is fixedly connected with the end cap. The screw slides over the friction pin and toward the end cap when a load is applied on the fracture device. The load required for further sliding of the screw over the friction pin increases incrementally as the screw slides towards the end cap.

10 Claims, 6 Drawing Sheets

U.S. PATENT DOCUMENTS

| | | | |
|---|---|---|---|
| 4,657,001 A | 4/1987 | Fixel | |
| 4,827,917 A | 5/1989 | Brumfield | |
| 4,940,467 A | 7/1990 | Tronzo | |
| RE33,348 E | 9/1990 | Lower | |
| 5,007,910 A | 4/1991 | Anapliotis et al. | |
| 5,032,125 A | 7/1991 | Durham et al. | |
| 5,041,116 A | 8/1991 | Wilson | |
| 5,116,336 A | 5/1992 | Frigg et al. | |
| 5,122,133 A | 6/1992 | Evans | |
| 5,167,663 A | 12/1992 | Brumfield | |
| 5,217,462 A | 6/1993 | Asnis et al. | |
| 5,429,641 A | 7/1995 | Gotfried | |
| 5,437,674 A | 8/1995 | Worcel et al. | |
| 5,514,138 A | 5/1996 | McCarthy | |
| 5,534,027 A | 7/1996 | Hodorek | |
| 5,578,034 A | 11/1996 | Estes | |
| 5,735,853 A | 4/1998 | Olerud et al. | |
| 5,743,912 A | 4/1998 | Lahille et al. | |
| 5,827,285 A | 10/1998 | Bramlet | |
| 5,871,485 A | 2/1999 | Rao et al. | |
| 5,899,906 A | 5/1999 | Schenk | |
| 5,904,683 A | 5/1999 | Pohndorf et al. | |
| 5,931,838 A | 8/1999 | Vito | |
| 5,976,139 A | 11/1999 | Bramlet | |
| 6,004,327 A | 12/1999 | Asnis et al. | |
| 6,139,552 A * | 10/2000 | Horiuchi | 606/88 |
| 6,183,474 B1 | 2/2001 | Bramlet et al. | |
| 6,187,007 B1 | 2/2001 | Frigg et al. | |
| 6,224,606 B1 | 5/2001 | Horiuchi | |
| 6,235,033 B1 | 5/2001 | Brace et al. | |
| 6,383,227 B1 | 5/2002 | Baroud et al. | |
| 6,402,755 B1 | 6/2002 | Pisharodi | |
| 6,454,769 B2 | 9/2002 | Wagner et al. | |
| 6,468,278 B1 | 10/2002 | Muckter | |
| 6,511,481 B2 | 1/2003 | von Hoffmann et al. | |
| 6,527,776 B1 | 3/2003 | Michelson | |
| 6,533,789 B1 | 3/2003 | Hall, IV et al. | |
| 6,592,586 B1 | 7/2003 | Michelson | |
| 6,595,993 B2 | 7/2003 | Donno et al. | |
| 6,599,290 B2 | 7/2003 | Bailey et al. | |
| 6,602,255 B1 | 8/2003 | Campbell et al. | |
| 6,620,163 B1 | 9/2003 | Michelson | |
| 6,632,224 B2 | 10/2003 | Cachia et al. | |
| 6,645,209 B2 | 11/2003 | Hall, IV et al. | |
| 6,679,883 B2 | 1/2004 | Hawkes et al. | |
| 6,685,706 B2 | 2/2004 | Padget et al. | |
| 6,717,214 B2 | 4/2004 | Pettruzello et al. | |
| 6,887,243 B2 | 5/2005 | Culbert | |
| 6,890,333 B2 | 5/2005 | von Hoffmann et al. | |
| 6,902,567 B2 | 6/2005 | Del Medico et al. | |
| 6,908,465 B2 | 6/2005 | von Hoffmann et al. | |
| 6,942,668 B2 | 9/2005 | Padget et al. | |
| 6,951,561 B2 | 10/2005 | Warren et al. | |
| 6,997,243 B2 | 2/2006 | Hsu et al. | |
| 7,001,389 B1 | 2/2006 | Navarro et al. | |
| 7,048,739 B2 | 5/2006 | Konieczynski et al. | |
| 7,070,601 B2 | 7/2006 | Culbert et al. | |
| 7,081,117 B2 | 7/2006 | Bono et al. | |
| 7,105,029 B2 | 9/2006 | Doubler et al. | |
| 7,135,023 B2 | 11/2006 | Watkins et al. | |
| 7,135,028 B2 | 11/2006 | Sugimura et al. | |
| 7,273,481 B2 | 9/2007 | Lombardo et al. | |
| 7,326,211 B2 | 2/2008 | Padget et al. | |
| 7,556,629 B2 | 7/2009 | von Hoffmann et al. | |
| 7,699,880 B2 | 4/2010 | Orbay et al. | |
| 7,846,190 B2 | 12/2010 | Ball | |
| 7,935,137 B2 | 5/2011 | Gorhan et al. | |
| 7,942,913 B2 | 5/2011 | Ziolo et al. | |
| 7,972,366 B2 | 7/2011 | Richelsoph et al. | |
| 2001/0049528 A1 | 12/2001 | Kubota | |
| 2002/0049445 A1 | 4/2002 | Hall et al. | |
| 2002/0143333 A1 | 10/2002 | von Hoffmann et al. | |
| 2002/0143334 A1 | 10/2002 | Hoffmann et al. | |
| 2002/0198527 A1 | 12/2002 | Muckter | |
| 2003/0069582 A1 | 4/2003 | Culbert | |
| 2003/0083660 A1 | 5/2003 | Orbay | |
| 2003/0097132 A1 | 5/2003 | Padget et al. | |
| 2003/0187440 A1 | 10/2003 | Richelsoph et al. | |
| 2004/0019353 A1 | 1/2004 | Freid et al. | |
| 2004/0030339 A1 | 2/2004 | Wack et al. | |
| 2004/0030340 A1 | 2/2004 | Pisharodi | |
| 2004/0127896 A1 | 7/2004 | Lombardo et al. | |
| 2004/0127899 A1 | 7/2004 | Konieczynski et al. | |
| 2004/0181222 A1 | 9/2004 | Culbert et al. | |
| 2004/0199162 A1 | 10/2004 | von Hoffmann et al. | |
| 2004/0220572 A1 | 11/2004 | Michelson | |
| 2004/0225289 A1 | 11/2004 | Biedermann et al. | |
| 2004/0236335 A1 | 11/2004 | Michelson | |
| 2005/0015089 A1 * | 1/2005 | Young et al. | 606/69 |
| 2005/0015131 A1 | 1/2005 | Fourcault et al. | |
| 2005/0096657 A1 | 5/2005 | Autericque et al. | |
| 2005/0131411 A1 | 6/2005 | Culbert | |
| 2005/0143735 A1 | 6/2005 | Kyle | |
| 2005/0143742 A1 | 6/2005 | Porcher | |
| 2005/0228386 A1 | 10/2005 | Ziolo et al. | |
| 2005/0234457 A1 * | 10/2005 | James et al. | 606/69 |
| 2005/0251137 A1 | 11/2005 | Ball | |
| 2005/0251142 A1 | 11/2005 | Hoffmann et al. | |
| 2006/0155281 A1 | 7/2006 | Kaup et al. | |
| 2006/0214606 A1 | 9/2006 | Kimura et al. | |
| 2006/0217711 A1 | 9/2006 | Stevens et al. | |
| 2006/0241606 A1 | 10/2006 | Vachtenberg et al. | |
| 2006/0241616 A1 | 10/2006 | Konieczynski et al. | |
| 2006/0241618 A1 | 10/2006 | Gasser et al. | |
| 2007/0162011 A1 | 7/2007 | Leyden et al. | |
| 2007/0260248 A1 | 11/2007 | Tipirneni | |
| 2008/0119855 A1 * | 5/2008 | Hoegerle et al. | 606/65 |
| 2008/0177330 A1 | 7/2008 | Ralph et al. | |
| 2008/0255559 A1 * | 10/2008 | Leyden et al. | 606/62 |
| 2008/0269807 A1 | 10/2008 | Simon et al. | |
| 2008/0275508 A1 * | 11/2008 | Haidukewych | 606/280 |
| 2009/0254129 A1 | 10/2009 | Tipirneni et al. | |
| 2009/0264885 A1 | 10/2009 | Grant et al. | |
| 2010/0174285 A1 | 7/2010 | Probe | |
| 2010/0312245 A1 | 12/2010 | Tipirneni et al. | |

FOREIGN PATENT DOCUMENTS

| | | |
|---|---|---|
| DE | 1225812 B | 9/1966 |
| DE | 8900121 U1 | 2/1990 |
| DE | 195 05 609 A1 | 8/1996 |
| DE | 19504115 A1 | 8/1996 |
| DE | 29709725 U1 | 8/1997 |
| DE | 29908360 U1 | 9/2000 |
| DE | 102005007674 B4 | 2/2007 |
| EP | 0482875 A1 | 4/1992 |
| EP | 0 321 170 B1 | 11/1994 |
| EP | 807420 | 11/1997 |
| EP | 0617927 B1 | 1/1999 |
| EP | 0668059 B1 | 1/2000 |
| EP | 988833 | 3/2000 |
| EP | 1486175 | 12/2004 |
| FR | 2674119 | 9/1992 |
| FR | 2832308 | 5/2003 |
| JP | 06125918 A | 5/1994 |
| JP | 06245941 A | 9/1994 |
| JP | 8322848 A | 12/1996 |
| JP | 2001149379 | 6/2001 |
| JP | 2002-360599 | 12/2002 |
| WO | 01/03592 | 1/2001 |
| WO | 0067652 B1 | 11/2001 |
| WO | 2004006792 | 1/2004 |
| WO | WO 2006087159 A1 * | 8/2006 |
| WO | 07138062 A1 | 12/2007 |

* cited by examiner

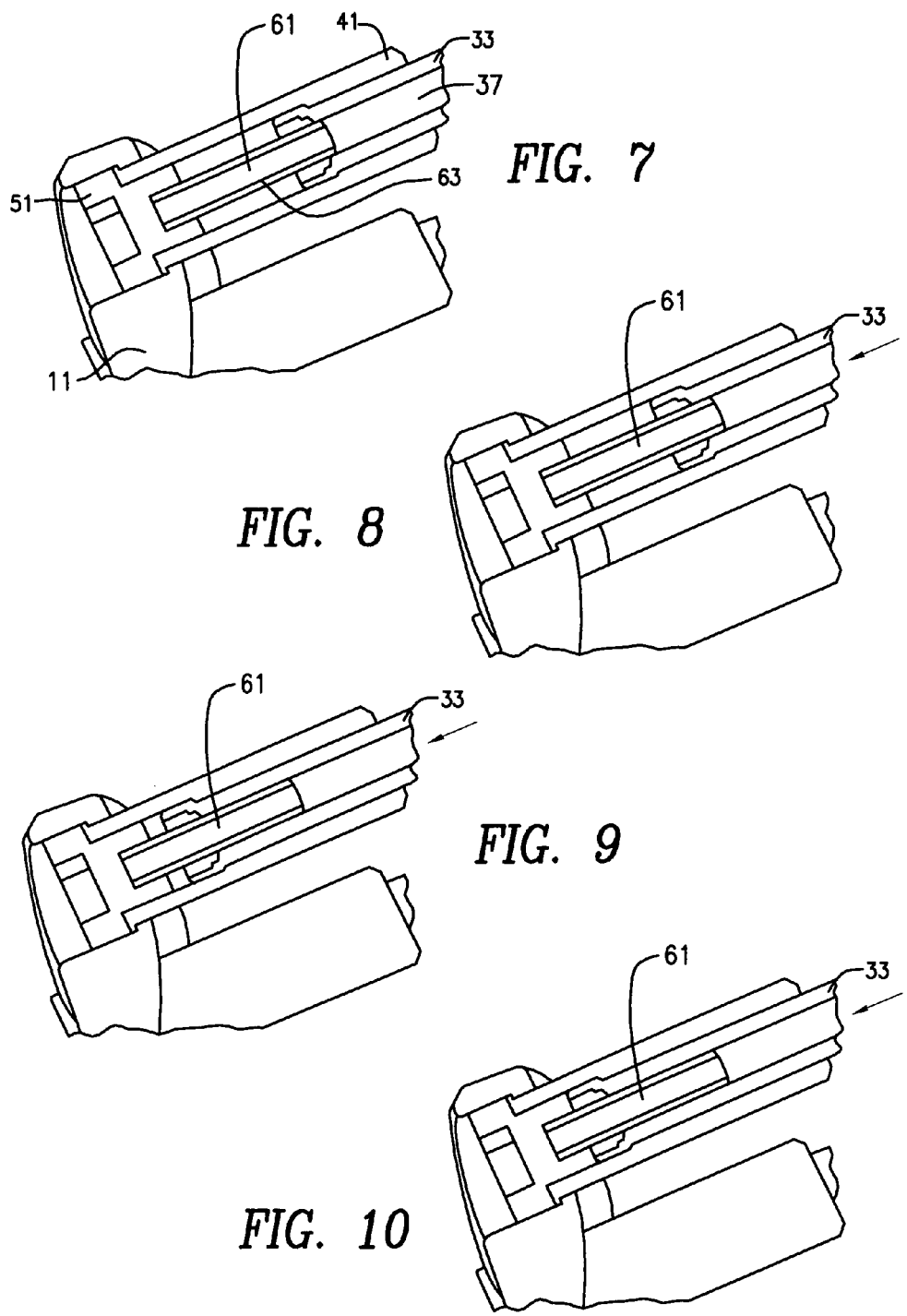

HIP FRACTURE DEVICE WITH BARREL AND END CAP FOR LOAD CONTROL

CROSS-REFERENCE TO RELATED APPLICATION

This application claims the benefit of the filing date of U.S. Provisional Patent Application No. 60/925,399 filed Apr. 19, 2007, the disclosure of which is hereby incorporated herein by reference.

FIELD OF THE INVENTION

The present invention relates generally to an apparatus and method for the treatment of fractures of the proximal femur including the neck of the femur and the intertrochantric region.

BRIEF DESCRIPTION OF THE PRIOR ART

Referring to FIG. 1, the femur 1, otherwise known as the thigh bone, generally comprises an elongate shaft extending from the hip to the knee. The proximal end of the shaft 3 includes a head 5, a neck 7, a greater trochanter 8 and a lesser trochanter 9. Internal fixation of femoral fractures in general is one of the most common orthopedic surgical procedures. Fractures of the proximal portion of the femur (hip fractures) generally include femoral neck fractures and intertrochanteric fractures. Fractures of the femur which extend into the neck of the bone are often treated with screws that thread into the femoral head and extend generally parallel to the femoral neck axis A-A to a plate on the lateral side of the shaft 3.

A conventional fracture fixation system for femoral neck fracture is disclosed in U.S. Pat. No. 3,107,666 (the '666 Patent). The fracture fixation system of the '666 Patent has a sleeve and a nail that is inserted in the sleeve. A plastic ring is disposed between the sleeve and the nail. The plastic ring frictionally engages the internal cylindrical surface of the sleeve and the external surface of the nail. The friction creates resistance to relative movement between the sleeve and the nail. However, upon the force acting on the system exceeding a threshold, relative movement between nail and sleeve is permitted.

Other conventional screw and plate systems typically apply a static compressive force across the fracture. It has been found that allowing the screw to travel along its axis in response to loading by the patient further encourages the growth of strong bone to heal the fracture. Screws of this type, known as dynamic compression screws, must provide axial movement while preventing angular rotation or lateral movement across the fracture. One shortcoming of dynamic compression screws is that unless the travel is appropriately limited, the neck of the femur may be undesirably shortened. Therefore, it is desirable to adjustably control the extent of axial movement (distance limited dynamization) and to adjustably provide a force that resists travel (load controlled dynamization). It is especially advantageous if the resisting force increases with the extent of travel.

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

SUMMARY OF THE INVENTION

The present invention fills the need described above by providing hip fracture devices allowing distance limited dynamization, load controlled dynamization and the combination of the distance limited dynamization and load controlled dynamization and methods of using these devices.

The hip fracture device has a plate and screw assembly. By replacement of modular components in the screw assembly the extent of axial travel and the force resisting travel may be adjusted interoperatively.

In one aspect of the present invention, the hip fracture device uses a fixed barrel and modular end caps to variably limit the extent of axial travel of the screw within the barrel while restraining the screw to be coaxial with the barrel.

In another aspect of the invention, a friction pin mounted to an end cap progressively engages a bore in the screw to provide load controlled dynamazation.

In another aspect of the invention, the hip fracture device includes a plate having a head portion and a shaft portion. A barrel projects from the head portion of the plate and a screw is inserted in the barrel. A friction pin is slidably connected with the screw, and an end cap is fixed to the head portion of the plate. The friction pin is fixedly connected with the end cap. The screw slides over the friction pin and toward the end cap when a load is applied on the fracture device. The load required for further sliding of the screw over the friction pin increases incrementally as the screw slides towards the end cap.

Another aspect of the invention is a method of repairing a fracture between the head and neck of a femur. The method includes the steps of affixing a plate having a head portion and a shaft portion on the femur, the plate having openings in the head portion and the shaft portion. A barrel is inserted in the opening in the head portion and a screw is inserted in the barrel. An end cap is inserted in the opening having the barrel inserted therein, and a friction pin is inserted between the end cap and the screw. The screw can slide over the friction pin and towards the end cap, and the load required for further sliding of the screw over the friction pin increases incrementally as the screw slides towards the end cap.

In another aspect, the invention provides a kit for repairing a fracture between the head and neck. The kit includes at least one plate, the plate having a head portion and a shaft portion, and openings formed in the head portion and the shaft portion. The kit also includes at least one barrel configured for insertion in the opening in the head portion, and at least two screws each having a central bore, each bore having a different diameter. Also included are at least two friction pins, each pin having an external diameter that matches the diameter of one of the central bore in one of the screw, and at least two end caps, each end cap having a first bore that matches the diameter of one of the friction pins.

BRIEF DESCRIPTION OF THE DRAWINGS

FIG. 7 is a view as in FIG. 2 showing the friction pin engaged in the end cap and the hip screw with the hip screw at the farthest distance from the end cap.

FIG. 8 is a view as in FIG. 2 showing the friction pin engaged in the end cap and the hip screw with the hip screw having moved axially towards the end cap.

FIG. 9 shows the hip screw after it has moved further axially towards the end cap as compared to the position shown in FIG. 8.

FIG. 10 shows the hip screw after it has moved farthest axially towards the end cap such that the top of the hip screw is touching the end cap and cannot move any further.

DETAILED DESCRIPTION OF THE PREFERRED EMBODIMENTS

Figure 1:
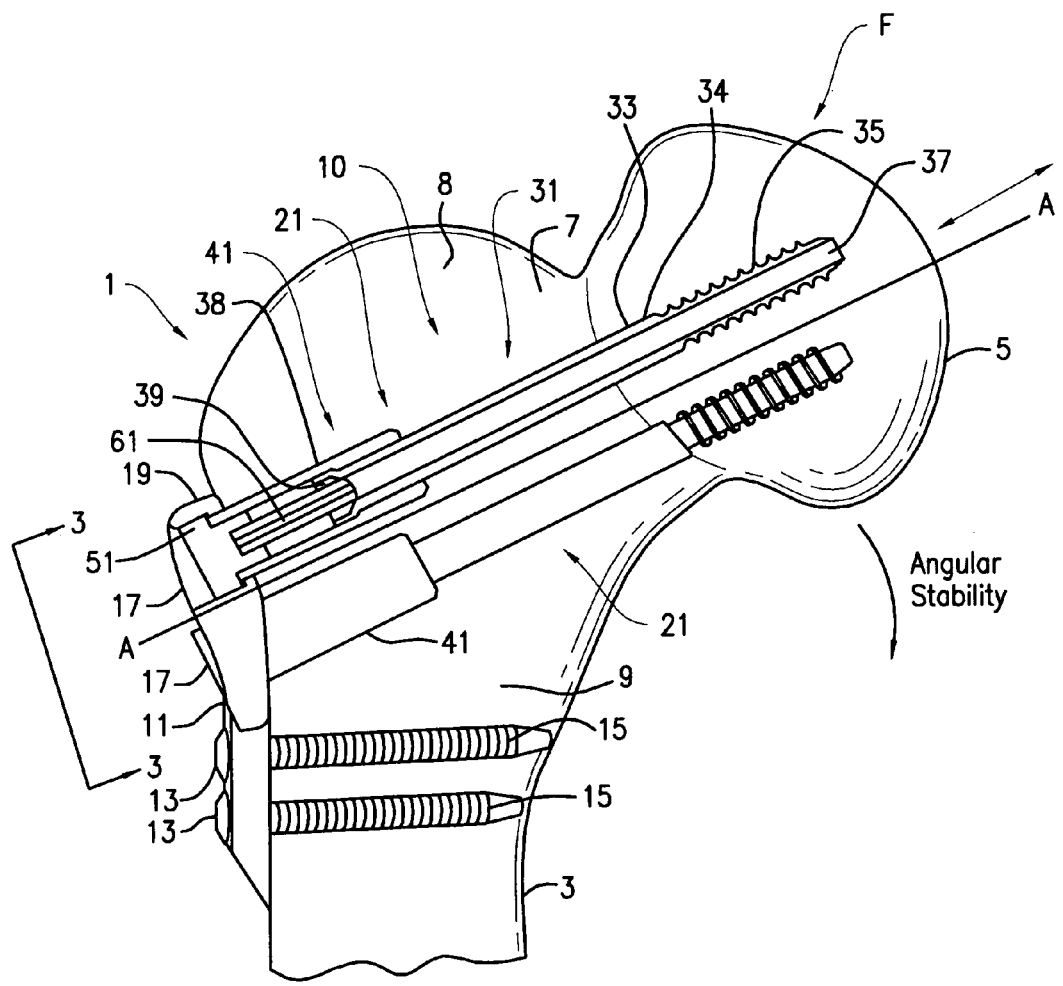
FIG. 1 is a frontal elevation view of a hip fracture device implanted in a proximal femur.

Referring to FIG. 1, a hip fracture device 21 includes a locking plate 11 and one of more (preferably three) screw assemblies 31. The hip fracture device 21 may be used for fixing bone fractures, particularly femoral neck fractures including Gaarden III/IV type fractures.

Figure 1A:
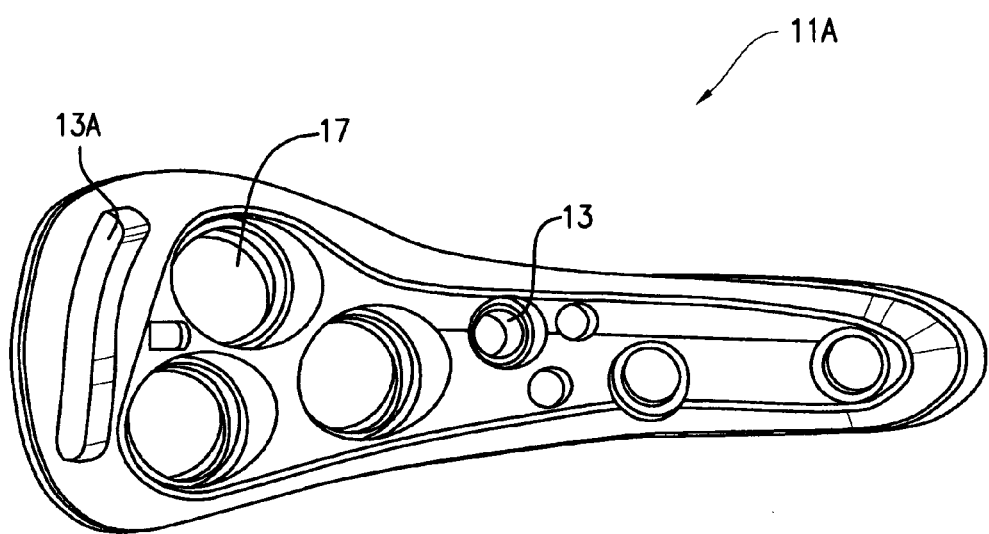
FIG. 1A shows another embodiment of a bone plate that may be used with the hip fracture device of FIG. 1.

The locking plate 11 generally conforms to the lateral portion of the proximal femur 1 and is attached to the femur by at least one cortical interlocking screw 15 passing through holes 13 in the subtrochanteric shaft region 3 of the femur 1. The interlocking screws 15 serve to attach the plate 11 to the femur 1. The plate 11 also has one or more stepped bores 17 for each screw assembly 31. The major diameter of the stepped bore 17 incorporates a screw thread for fastening the screw assembly 31. The minor diameter of the stepped bore 17 creates a shoulder 19 at the junction of the major and minor diameters. Each stepped bore 17 is aligned with the axis of each of the screw assemblies 31. FIG. 1A shows a plate 11A. Plate 11A is a variation of design of plate 11, and includes a slot 13A. Plate 11A may be used in place of plate 11. A guide wire may be inserted through slot 13A and into the femur 1. The guide wire may be used to position the plate 11A in a desired alignment on the surface of the femur 1. The compression screw embodiments disclosed hereafter may be used with the bone plate 11A.

The screw assemblies 31 incorporate a hip screw 33, a barrel 41, an end cap 51 and an optional friction pin 61. The friction pin may also be referred to as a spring pin. At least one screw assembly 31, in conjunction with the plate 11, provides angular stability in the indicated direction to counteract the moment created on the femoral neck 7 by the normal force F resulting from loads on the femoral head 5. The screw assembly 31 also provides angular stability in all other directions. Rotational stability about the head axis A-A is achieved if more than one screw assembly 31 is connected to the plate 11. Typically the hip screw assembles 31 are oriented parallel to the femoral neck axis A-A as shown.

Hip screw 33 is typically cannulated with a bore 37. Non-cannulated versions may have a blind bore 37 at the distal end. The screw 33 has a central shaft 34 defining a minor external diameter and an external flange 38 defining a major external diameter at the distal end of the screw. Formed internal to flange 38 are rotational features such as a hex socket 39. Threads 35, suitable for anchoring to bone, are formed at the proximal end of the screw 33 and engage the cancelleous bone of the femoral head 5.

Figure 2:
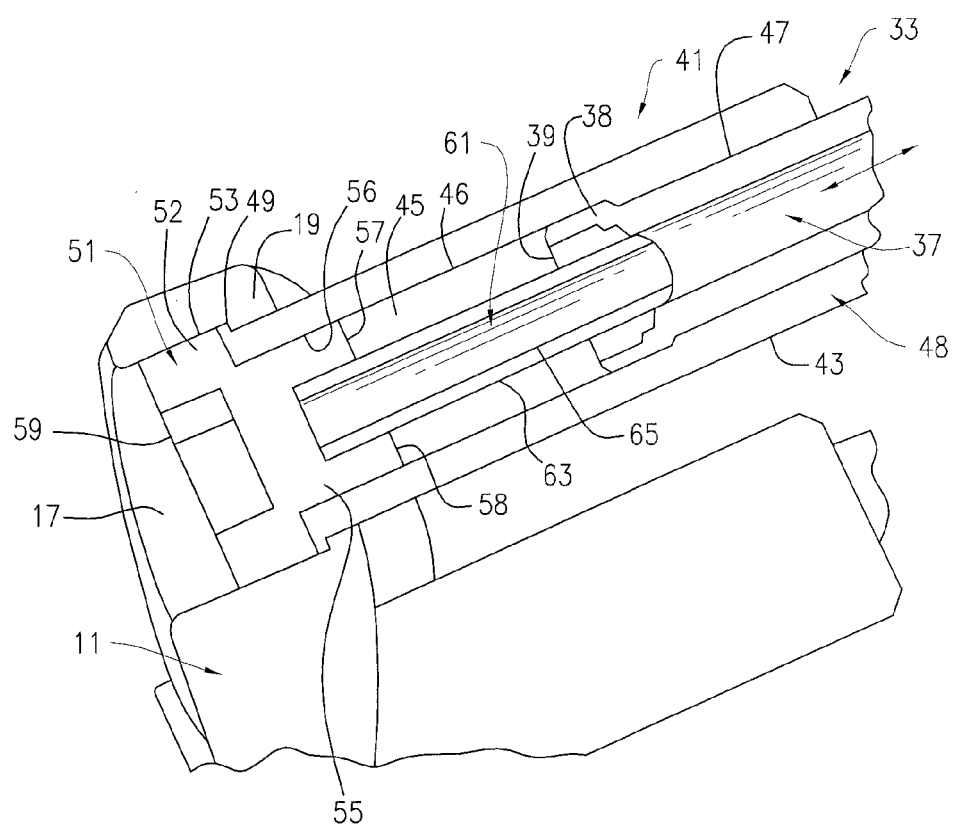
FIG. 2 is a close up view of a portion of FIG. 1.

Referring to FIG. 2, barrel 41 is generally cylindrical in shape with an external diameter 43 corresponding to the minor diameter of the stepped bore 17 in plate 11. The barrel 41 has a sliding fit in the stepped bore 17 and rests on the shoulder 19. Located at the distal end of barrel 41 is an external flange 49 that is a sliding fit with the major diameter of stepped bore 17 and engages shoulder 19 to prevent movement of the barrel 41 in the proximal direction along the screw assembly axis. The barrel 41 has a stepped bore 45 with major diameter 46 and minor diameter 47. The minor diameter 47 creates a shoulder 48 at the junction of the major diameter 46 and minor diameter 47. The minor diameter 47 is a sliding fit with central shaft 34 of the screw 33 and the shoulder 48 engages the external flange 38 to limit movement of the screw 33 in the proximal direction along the screw assembly axis.

A head 52 is formed in a distal portion of the end cap 51. The head 52 has a major diameter 53 and external machine threads formed on the major diameter 53 for fastening with the mating threads of the bore 17 of the plate 11. Formed internal to head 52 are rotational features such as a hex socket 59. The proximal region of the end cap 51 is a shaft 55 with a minor diameter 56 providing a slip fit with major diameter 46 of the barrel 41. The shaft 55 has a proximal end 58 which may abut the end of the flange 38 to limit movement of the screw 33 in the distal direction along the screw assembly axis. The end 58 has a blind bore 57.

The friction pin 61 is provided for load controlled dynamization. The friction pin 61 is typically a roll pin with a slot 67 (FIG. 3) that, when present, is press fit in bore 57 and is also a sliding interference fit with the bore 37 of the screw 33. The bore 57 is sized to firmly retain the friction pin. The bore 37 is sized to provide a controlled frictional resistance to resist movement of the screw 33 in the distal direction along the screw assembly axis as will be further described in conjunction with FIGS. 7-10.

Figure 3:
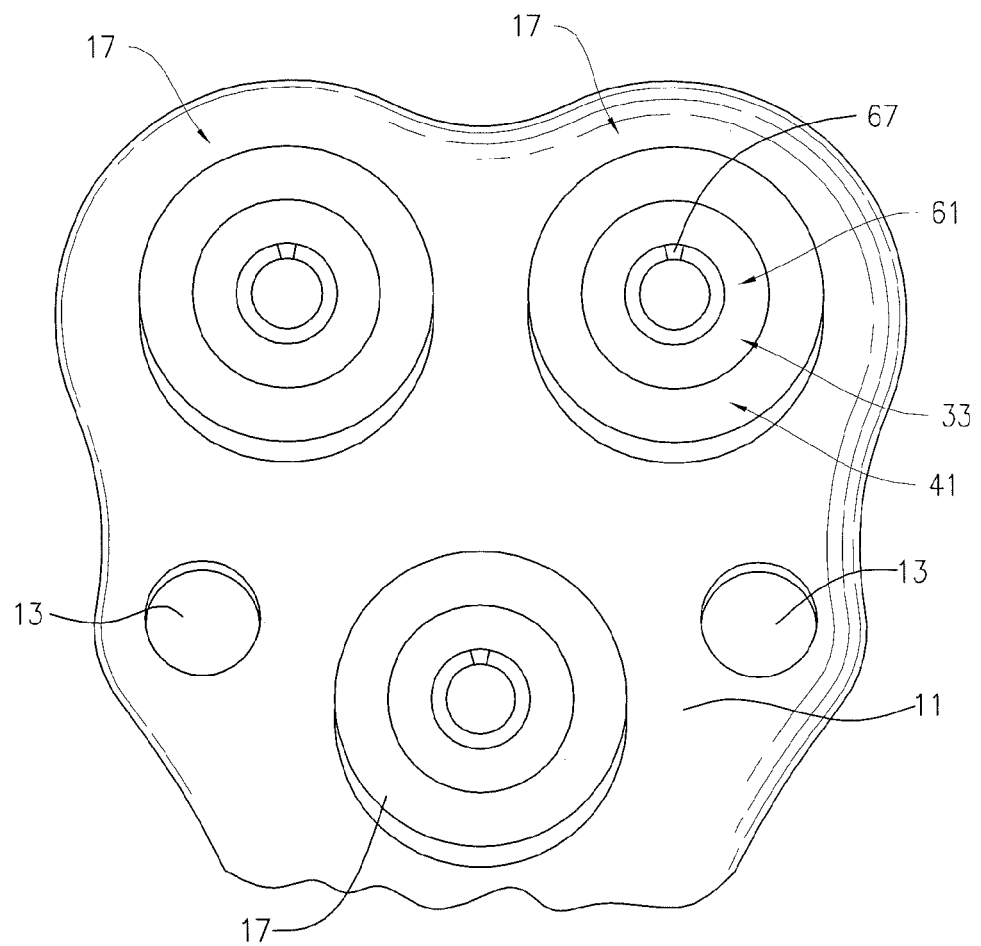
FIG. 3 is a sectional lateral view as shown in FIG. 1 with the end cap removed.

All the various diameters and bores of the screw assembly 31 are concentric about the axis of the assembly as depicted in FIG. 3, which does not show the end caps 51 or the hex socket 39. The various concentric sliding fits allow the screw 33 to move only along its axis, that is, parallel to the axis A-A.

Assembly of the device 21 on femur 1 proceeds as follows. First, the plate 11 is fixed at the proximal femur 1 at the lateral region of the shaft 3. The femur 1 is prepared by drilling holes sized for insertion of the screw 31 and the barrel 41. The barrel 41 is then inserted into the bore 17 of the plate 11 until its final position where the flange 49 is seated against the shoulder 19 formed between the major and minor diameters of the bore 17. The screw 33 is then inserted into the barrel 41 and turned into the bone until the screw flange 38 is seated against the barrel shoulder 48. By turning several additional turns of the compression screw 33 a femoral head fragment that includes the femoral head 5 is pulled against the distal fracture surface of the femur 1 and the fracture is initially compressed.

Figure 4:
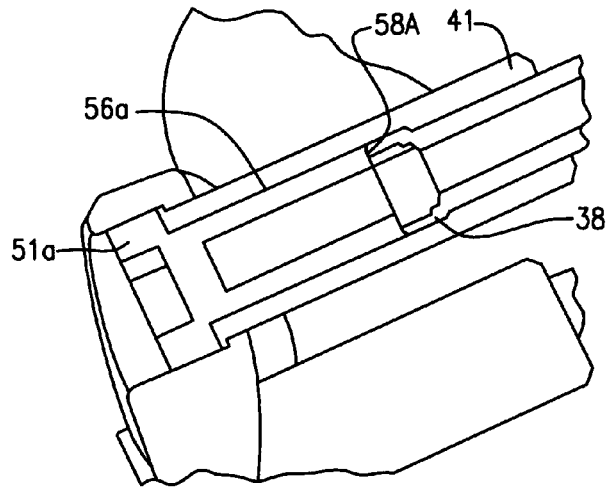
FIG. 4 is a view as in FIG. 2 showing an end cap with a long shaft.
Figure 5:
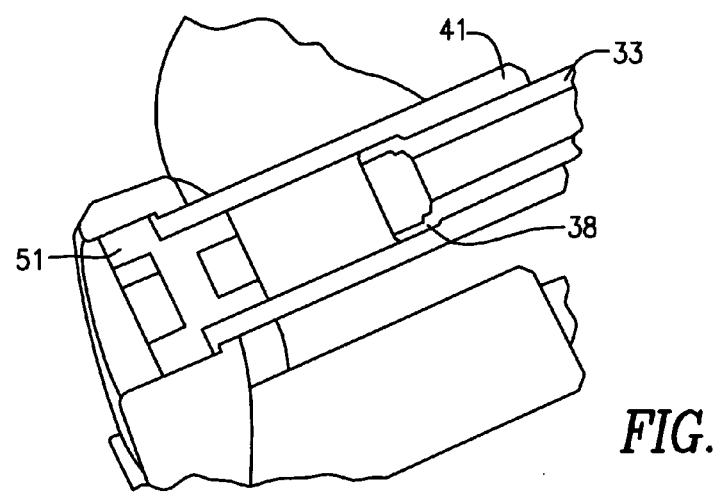
FIG. 5 is a view as in FIG. 2 showing an end cap with a short shaft.

By selecting from a kit of various configurations of end caps 51 and friction pins 61, the extent and force required for dynamization can be adjusted by the surgeon at this point in the operation. Should the surgeon desire static locking of the fragment in order to strictly limit travel and prevent shortening of the femoral neck, an end cap 51a with a longer shaft having minor diameter 56a is used to prevent distal motion of the screw 33 as shown in FIG. 4. Here the end cap 51a is in contact with the end of screw 33 and therefore no axial movement of the femoral head fragment is allowed. FIGS. 4 and 5 show how caps 51a, 51 with various lengths of shaft may be used to allow distance limited sliding of the screw 33. In FIG. 5, there is a space between the end of the end cap 51 and the opposing end of the screw 33. Therefore, the screw 33 and consequently the femoral head fragment can move axially towards the cap end 51. The maximum travel in this case is equal to the space between the end of the end cap 51 and the opposing end of the screw 33. This distance limited sliding of the femoral head fragment allows for fragment opposition and postoperative dynamic fracture site compression by weight bearing while limiting excessive femoral neck shortening.

Figure 6:
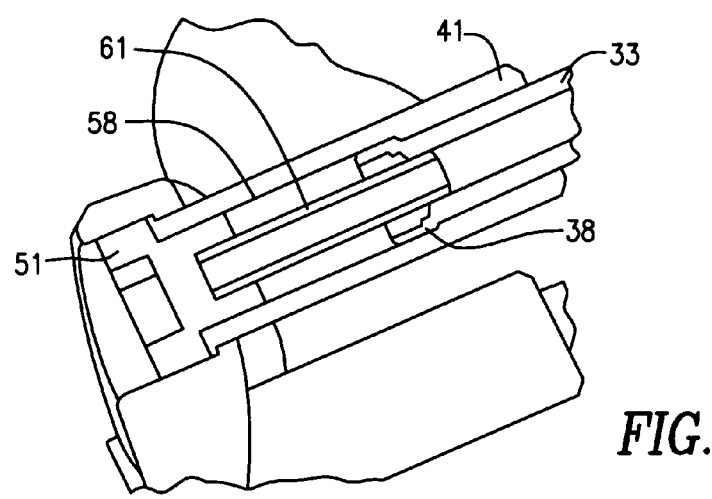
FIG. 6 is a view as in FIG. 2 showing a friction pin placed between an end cap and a hip screw.

As shown in FIG. 6, when friction pin 61 is added, the screw assembly 31 provides load controlled sliding of the screw 33. This sliding allows femoral head fragment opposition and postoperative dynamic fracture site compression by weight bearing while limiting the load on the fracture site, limiting the travel based on the load, and preventing stress induced resorption of the bone. The initial friction created by the friction pin 61 and the bore 37 can be varied by selecting from a kit of pins with varying diameters according to the patients weight, bone structure and the type of fracture. Thus, a heavier patient with larger bones may be fitted with a pin that creates more friction.

The hip fracture device 21 shown in FIG. 6 provides load controlled sliding of the femoral head fragment in order to allow for fragment apposition and postoperative dynamic fracture site compression by weight bearing while limiting the load on the fracture site and preventing stress induced resorption of the bone. The control mechanism provides increasing resistance with increasing sliding distance. This is caused by the progressively greater length of the friction pin 61 engaged by the bore 37 during sliding as depicted in FIGS. 7-10. Sliding of screw 33 stops when either the resistance becomes equal to the body weight induced force or when the distance limit is reached.

When multiple screw assemblies 31 are used, the installation steps are repeated and the resistance may be varied by using the friction pins in some or all of the assemblies. Typically, the distance limits are the same for all the assemblies.

In use, the plate 11 is fixed to the bone by inserting cortical screws 15 through holes 13 and into the subtrochantric shaft region. Using methods known to one skilled in the art, one or more stepped holes are drilled from the lateral side of femur into the femoral head portion. The holes are sized to accept screw 33 and barrel 41. Next, a barrel 41 is inserted in a hole 13 and a screw 33 is inserted in the barrel. If more then one screws are to be used, the process may be repeated at this time or later. Next, the screw 33 is rotated in the femoral head fragment thereby attaching it to the fragment. The rotation is continued after the screw 33 has bottomed on the shoulder 48 resulting in closing of the fracture gap. The screw may be rotated further to apply initial compression to the fracture site. Next, the end cap 51a (FIG. 4) is inserted in the hole 13 and screwed in place. The end cap 51a may be of such length that its proximal end rests on the end of the screw 33 to prevent any axial movement of screw 33. If the end cap is of a shorter length, the screw 33 would be allowed to slide back in axial direction. The sliding movement would be stopped when the screw 33 touches the end cap 51.

Alternatively, as shown in FIG. 7, one end of the friction pin 61 is inserted in the bore 37 of the screw 33 and the other end is inserted in the bore 57 of end cap 51, thereby clamping the friction pin 61 between the end cap 51 and screw 33. Upon application of load, for example, by putting body weight on the hip and thus device 21, the friction pin 61 may be pushed further into the bore 37. As the friction pin 61 is pushed further in the bore 37, as seen in FIGS. 8 and 9, increasingly greater load is required for axial movement of the screw 33 towards cap 51. Once the screw 33 touches the end cap 51, as seen in FIG. 10, any further axial travel of the screw 33 is prevented.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention.

The invention claimed is:

1. A hip fracture device comprising:
a plate, the plate having a head portion and a shaft portion;
a barrel projecting from the head portion of the plate;
a screw inserted in the barrel;
a threadless friction pin adapted to slide within the screw; and
an end cap fixed to the head portion of the plate, wherein the friction pin is fixedly connected with the end cap, and the screw slides over the friction pin and toward the end cap when a load is applied on the fracture device, wherein the load required for sliding of the screw over the friction pin increases as the screw slides towards the end cap.

2. The device of claim 1, wherein the threadless friction pin comprises:
a tubular body; and
a slit formed in the tubular body.

3. The device of claim 2, wherein the end cap comprises:
a head; and
a shaft projecting from the head, the shaft having a blind bore sized to form a press fit with the external surface of the friction pin.

4. The device of claim 3, further comprising:
first threads formed on the head; and
second threads formed in a bore in the head portion of the plate, the first and the second threads configured to mate, thereby fixing the end cap to the plate.

5. The device of claim 3, wherein the maximum length of travel of the screw toward the end cap is inversely proportional to the length of the shaft projecting from the head.

6. The device of claim 3, wherein the screw further comprises a flange and the barrel comprises a shoulder, and the flange rests against the shoulder when the screw is at the farthest distance possible from the end cap.

7. The device of claim 6, wherein rotating the screw when the flange is resting against the shoulder pulls a femoral head fragment towards a femur to close a gap between them.

8. The device of claim 1, further comprising;
a second and a third barrel projecting from the head of the plate;
a second screw inserted in the second barrel and a third screw inserted in the third barrel;
a second friction pin adapted to slide within the second screw and a third friction pin adapted to slide within the third screw; and
a second and a third end caps fixed to the head portion of the plate, wherein the second friction pin is fixedly connected with the second end cap and the third friction pin is fixedly connected with the third end cap, and the second and the third screws slide over the second and the third friction pins respectively and toward the end cap when a load is applied on the fracture device.

9. The device of claim 8, wherein the load required for sliding of the screw, the second screw and the third screw over the friction pin, the second friction pin and the third friction pin respectively increases as the screws slide towards the respective end caps.

10. The device of claim 9, wherein the friction pin is of different diameter as compared to the second friction pin and the third friction pin.

* * * * *

UNITED STATES PATENT AND TRADEMARK OFFICE
CERTIFICATE OF CORRECTION

Page 1 of 1

PATENT NO. : 8,398,636 B2
APPLICATION NO. : 12/082691
DATED : March 19, 2013
INVENTOR(S) : Bernd Simon, Jakob Kemper and Carsten Hoffmann It is certified that error appears in the above-identified patent and that said Letters Patent is hereby corrected as shown below:

In the Specification

Col. 2, Line 54, "bore" should read --bores--.
Col. 2, Line 54, "screw" should read --screws--.
Col. 5, Line 18, "patients" should read --patient's--.
Col. 5, Line 40, after "of" insert --the--.
Col. 5, Line 43, "then" should read --than--.
Col. 5, Line 44, "screws are" should read --screw is--.

In the Claims

Col. 6, Line 61, claim 8, "caps" should read --cap--.

Signed and Sealed this
Thirty-first Day of March, 2015

Michelle K. Lee
*Director of the United States Patent and Trademark Office*